(12) United States Patent
Tsubouchi (10) Patent No.: US 11,090,034 B2
(45) Date of Patent: Aug. 17, 2021

(54) CIRCULAR RETRACTOR FOR CARDIOVASCULAR VALVE PROCEDURES

(71) Applicant: Terumo Cardiovascular Systems Corporation, Ann Arbor, MI (US)

(72) Inventor: Takeshi Tsubouchi, Dexter, MI (US)

(73) Assignee: TERUMO CARDIOVASCULAR SYSTEM CORPORATION, Ann Arbor, MI (US)

( * ) Notice: Subject to any disclaimer, the term of this patent is extended or adjusted under 35 U.S.C. 154(b) by 0 days.

(21) Appl. No.: 17/102,990

(22) Filed: Nov. 24, 2020

(65) Prior Publication Data

US 2021/0077086 A1 Mar. 18, 2021

Related U.S. Application Data

(63) Continuation of application No. PCT/US2019/036447, filed on Jun. 11, 2019.

(Continued)

(51) Int. Cl.
*A61B 17/02* (2006.01)
*A61B 17/00* (2006.01)

(52) U.S. Cl.
CPC ...... *A61B 17/0218* (2013.01); *A61B 17/0293* (2013.01); *A61B 2017/00243* (2013.01); *A61B 2017/0225* (2013.01)

(58) Field of Classification Search
CPC ............ A61B 17/0218; A61B 17/0293; A61B 2017/0243; A61B 2017/0225; A61B 2017/0237

See application file for complete search history.

(56) References Cited

U.S. PATENT DOCUMENTS 5,486,183 A * 1/1996 Middleman ........ A61B 17/0469
606/127
5,613,937 A * 3/1997 Garrison .......... A61B 17/00234
128/898

(Continued)

FOREIGN PATENT DOCUMENTS

DE       102012001500 A1   8/2013
WO    WO-2009034922 A1 *  3/2009  ............. A61B 17/32
WO    WO-2014115370 A1 *  7/2014  ......... A61B 17/0218

OTHER PUBLICATIONS

International Search Report, PCT/US2019/036447, dated Aug. 26, 2019.

*Primary Examiner* — Julianna N Harvey
*Assistant Examiner* — Emily Stiklickas
(74) *Attorney, Agent, or Firm* — Darryl Newell; MacMillan, Sobanski & Todd, LLC (57) ABSTRACT

A retractor is configured to manipulate for vascular structures during minimally invasive surgical procedures such as mitral valve repair. A long wire has a spring loop at one end surrounded by a helical spring coil forming a toroidal ring. The spring maintains a circular shape while expanding and shrinking under manual control to a desired size for initiating and maintaining the retraction. The looping end of the spring wire is enclosed by the helical coil spring. The other end of the long wire is mounted through a frame with two hollow support arms carrying separate sides of the long wire and guiding them through a long support tube to a proximal end of the tube where each separate portion of the long wire attaches to a coupler. The coupler includes a handle or other push/pull mechanism to adjust the size of toroidal ring.

11 Claims, 7 Drawing Sheets

Related U.S. Application Data (60) Provisional application No. 62/683,737, filed on Jun. 12, 2018.

(56) References Cited

U.S. PATENT DOCUMENTS

| | | | |
|---|---|---|---|
| 5,860,987 A * | 1/1999 | Ratcliff | A61B 17/0218 606/113 |
| 5,891,162 A * | 4/1999 | Sugarbaker | A61B 17/29 606/207 |
| D443,359 S | 6/2001 | Nathanson et al. | |
| 6,413,273 B1 * | 7/2002 | Baum | A61F 2/88 606/198 |
| 6,558,318 B1 | 5/2003 | Daniel et al. | |
| 7,871,374 B2 | 1/2011 | De Canniere et al. | |
| 7,922,657 B2 * | 4/2011 | Gillinov | A61B 17/02 600/210 |
| 10,117,700 B2 * | 11/2018 | Kadykowski | A61B 17/00008 |
| 2002/0013601 A1 * | 1/2002 | Nobles | A61M 29/02 606/193 |
| 2004/0260153 A1 * | 12/2004 | Pulford | A61B 17/0293 600/208 |
| 2005/0228232 A1 | 10/2005 | Gillinov et al. | |
| 2006/0074277 A1 * | 4/2006 | Yoshida | A61B 17/0218 600/209 |
| 2006/0089536 A1 | 4/2006 | Perez-Cruet et al. | |
| 2007/0078477 A1 * | 4/2007 | Heneveld, Sr. | A61M 29/02 606/191 |
| 2007/0088204 A1 | 4/2007 | Albrecht et al. | |
| 2011/0040371 A1 * | 2/2011 | Hanssen | A61F 2/88 623/1.22 |
| 2011/0046448 A1 | 2/2011 | Paolitto et al. | |
| 2011/0275902 A1 * | 11/2011 | Bucholz | A61B 17/0293 600/206 |
| 2012/0128701 A1 * | 5/2012 | Goodman | A61P 31/00 424/184.1 |
| 2013/0018228 A1 * | 1/2013 | Armstrong | A61B 17/0218 600/204 |
| 2013/0110231 A1 * | 5/2013 | Dobrilovic | A61B 17/0483 623/2.41 |
| 2013/0144311 A1 * | 6/2013 | Fung | A61B 17/12013 606/139 |
| 2014/0194698 A1 * | 7/2014 | Melsheimer | A61B 17/0281 600/233 |
| 2015/0119647 A1 * | 4/2015 | Vaillancourt | A61B 17/3423 600/208 |
| 2017/0128210 A1 | 5/2017 | Arcidi | |

\* cited by examiner

CIRCULAR RETRACTOR FOR CARDIOVASCULAR VALVE PROCEDURES

CROSS REFERENCE TO RELATED APPLICATIONS

This application is a continuation of PCT Application No. PCT/US2019/36447, filed Jun. 11, 2019, based on and claiming priority to U.S. Provisional Application Ser. No. 62/683,737, filed Jun. 12, 2018, both of which are incorporated herein by reference in their entirety.

BACKGROUND OF THE INVENTION

The present invention relates in general to a surgical retractor for holding open a valve (e.g., mitral valve) during valve surgery, and, more specifically, to an expandable loop insertable into a valve with a diameter of the loop being manually controllable.

Minimally-invasive cardiac surgery can be used to repair or replace cardiac valves such as the mitral valve. After an incision is made through an atrial wall, the atrial tissue needs to be retracted in order to provide sufficient access to the valve. Once the valve is accessed, it becomes important to hold open the valve to facilitate repair and/or replacement actions such as suturing of portions of the valve.

Mitral valve retraction in particular needs the ability to expand a perimeter of the valve when it is being accessed via a deep, narrow incision, with the valve positioned at a large distance from an incision hole. For example, a minimally invasive cardiac surgery (MICS) mitral repair procedure uses an access tunnel from a right side of the rib cage via a small incision hole to the mitral valve across the chest.

U.S. Pat. No. 7,871,374 shows one type of retractor device which has been applied in MICS surgery, but this device can be difficult to put through a small hole and to adjust to a proper opening from a remote location. There is also some difficulty in removing this retractor after the surgical tasks are completed because it does not have a self-retraction (i.e., shrinking) feature.

An object of the invention is to provide a retraction tool that is easy to insert and manipulate through a small incision hole and which can be adjusted to the necessary size and position very easily.

SUMMARY OF THE INVENTION

In a preferred embodiment of the invention, a long wire loop has a distal end surrounded by a spring wire formed into a toroidal ring and a proximal end connected to a handle. The toroidal ring is deployed inside an atrial surface to be retracted. Pushing and pulling the handle relative to the toroidal ring will expand and shrink the toroidal ring to a necessary size.

In one aspect of the invention, a surgical retractor for minimally invasive cardiac surgery comprises a toroidal ring comprised of a plurality of turns of an expandable helical spring. A control wire has a loop end disposed within the turns of the toroidal ring. A frame has 1) Y-arms at a distal end for guiding the control wire and holding ends of the loop end at an edge of the toroidal ring, and 2) a hollow shaft which slidably receives a proximal end of the control wire. A handle is anchored to the proximal end of the control wire and is movable with respect to the hollow shaft in order to slide the control wire to expand and contract the loop end, thereby adjusting the ring between an expanded state and a contracted state.

DETAILED DESCRIPTION OF PREFERRED EMBODIMENTS

The invention provides a secure and convenient method of retraction for vascular structures during MICS procedures such as mitral valve repair. A long wire has a spring loop at one end surrounded by helical spring coil forming a toroidal ring, wherein the spring maintains a desired circular shape while expanding and shrinking under manual control to a desired size for initiating and maintaining the retraction. The looping end of the spring wire can be coiled with one or more turns, with each turn enclosed by the helical coil spring. The other end of the long wire is mounted through a frame with two hollow support arms carrying separate sides of the long wire and guiding them through a long support tube to a proximal end of the tube where each separate portion of the long wire attaches to a coupler. The coupler includes a handle or other push/pull mechanism to adjust the size of toroidal ring.

Figure 1:
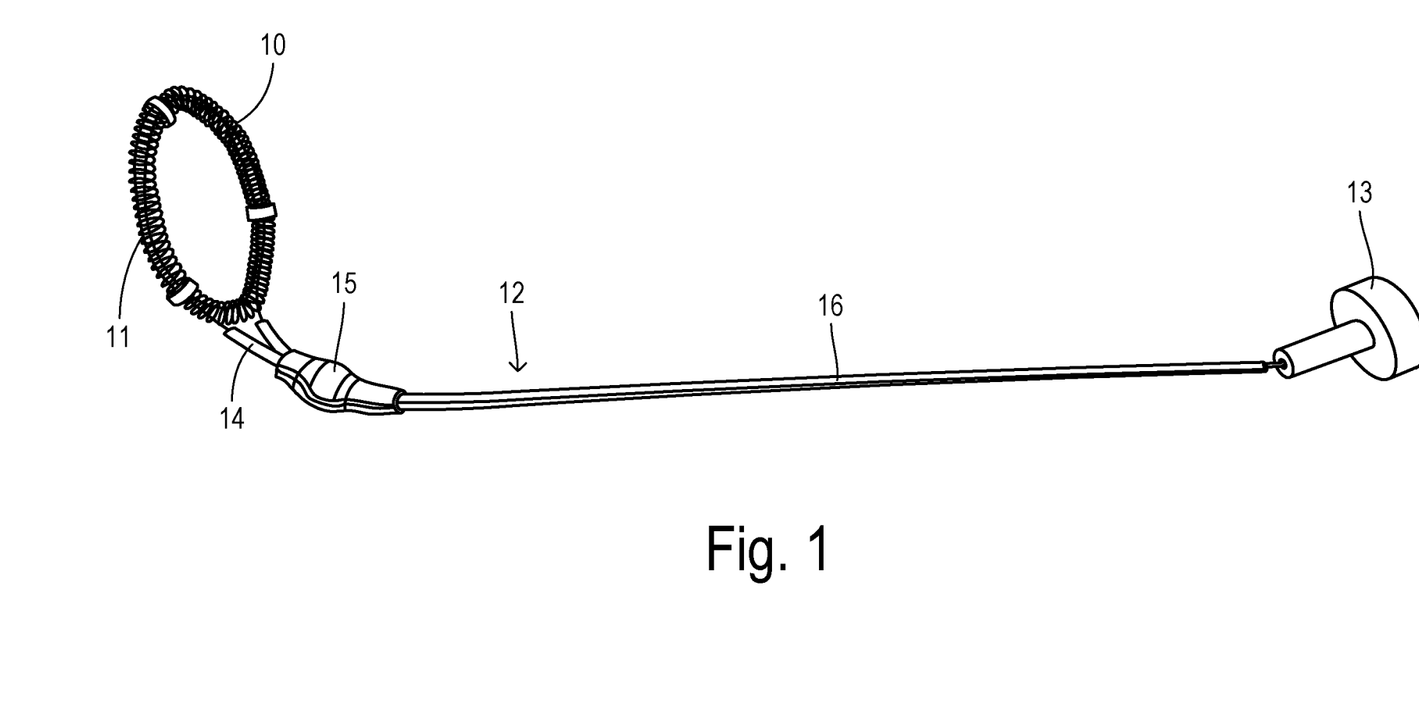
FIG. 1 is a side view of one preferred embodiment of a toroidal ring retractor in an expanded state.
Figure 2:
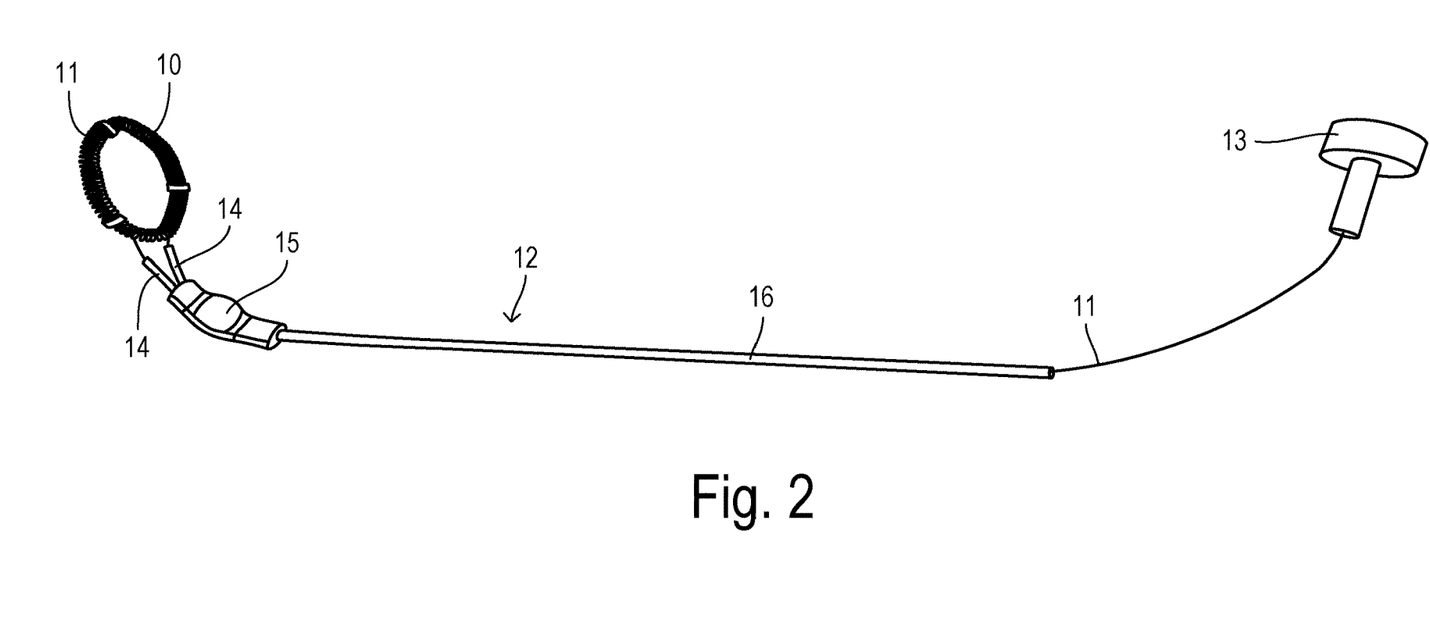
FIG. 2 is a side view of the toroidal ring retractor of FIG. 1 in a contracted state.

A first embodiment is shown in FIGS. 1 and 2. A coil spring 10 of a suitable diameter and length is formed into a circle (toroidal ring) by joining together the opposite ends of spring 10. Spring 10 is insertable into a cardiovascular valve (e.g., mitral valve) via a surgical opening while in a contracted state (i.e., minimal diameter of the ring) and can be adjustably expanded using the additional components described below.

A control wire 11 forms a loop end within spring ring 10 and has opposite sides extending from the loop end through a frame 12 to a handle 13 where both sides of wire 11 are anchored. Frame 12 has a pair of hollow Y-arms 14 extending from a hollow base 15 and a long hollow shaft 16 also mounted to base 15. Wire 11 extends through arms 14, base 15, and shaft 16 to attach to handle 13. Wire 11 is slidable within frame 12 by pushing or pulling on handle 13 so that the length of wire 11 accommodated within ring 10 is manually controlled, thereby changing the circumference of the loop end which acts on ring 10 to change its diameter. FIG. 2 shows handle 13 pulled away from shaft 16 which exposes a length of wire 11 between shaft 16 and handle 13. This shortens the length of wire 11 within the loop end inside ring 10 and shrinks ring 10 into its contracted state. By pushing handle 13 back toward shaft 16 so that wire 11 slides forward through shaft 16, the loop end within ring 10 enlarges, causing ring 10 to expand (e.g., so that it can hold open the mitral valve). Ring 10 maintains its circular profile whether it is expanded or contracted by the balancing of forces along its perimeter, provided that the ends of Y-arms 14 are fairly close together (i.e., extend over a short portion of the circumference of ring 10).

In order to properly position ring 10 at a desired location, the shape of frame 12 is preferably adjustable. Thus, shaft 16 and/or arms 14 may be made of a malleable tube material. Any malleable biocompatible metal or metal alloy can be used (e.g., stainless steel, titanium, or nickel-titanium), as well as resilient plastic material and composite or coated bodies.

Figure 3:
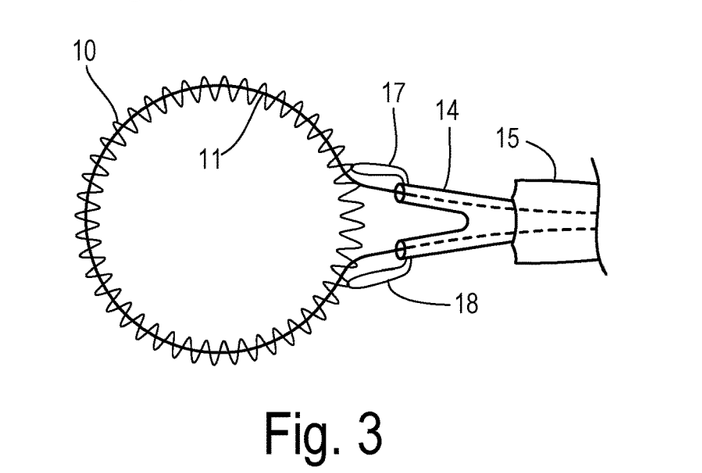
FIG. 3 is a top view showing the expanded state of FIG. 1 in greater detail.
Figure 4:
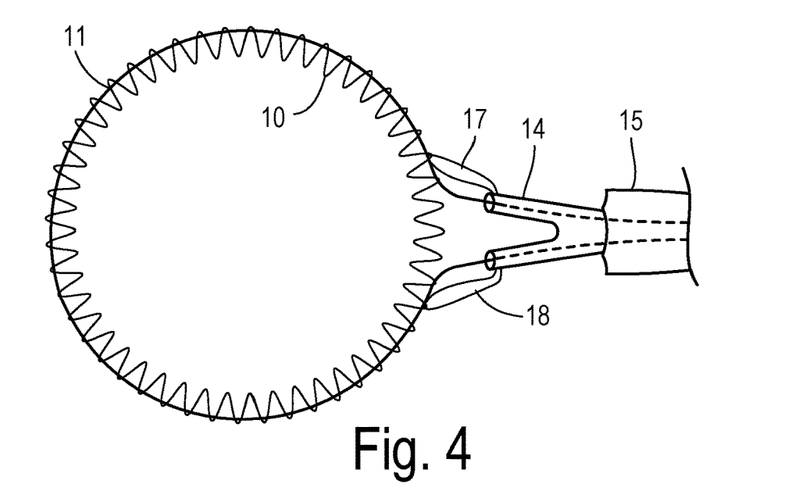
FIG. 4 is a top view showing the contracted state of FIG. 1 in greater detail.

FIGS. 3 and 4 show the contracted state and expanded state, respectively, in greater detail. In FIG. 3, the loop end of wire 11 rests within ring 10 so that ring 10 relaxes to its smallest configuration. In FIG. 4, an increased length of wire 11 is fed out via Y-arms 14 so that wire 11 presses outward against ring 10, thereby expanding ring 10 by a controlled distance. Each arm of arm unit 14 is anchored to a respective loop of the spring of ring 10 by a respective tether 17 and 18. Tethers 17 and 18 limit longitudinal movement of ring 10 away from the base which would otherwise keep ring 10 from expanding.

Figure 5:
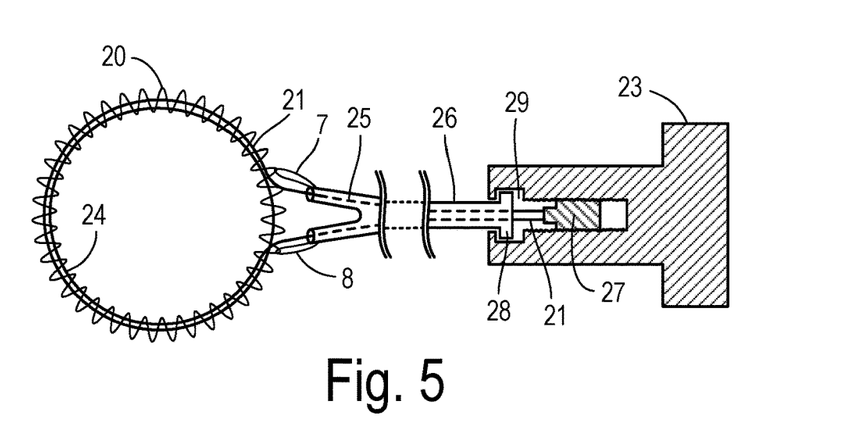
FIG. 5 is a top view showing another preferred embodiment of a toroidal ring retractor with a multi-loop control wire.

FIG. 5 shows another embodiment wherein a control wire 21 forms a loop end 24 within a toroidally-extending helical spring 20. Opposite sides of wire 21 extending from loop end 24 are threaded through a pair of hollow Y-arms 25 and a hollow shaft 26 to a handle 23 where both sides of wire 21 are anchored. Spring ring 20 is tethered to Y-arms 25 by tethers 7 and 8. In this embodiment, loop end 24 has two turns, which allows for finer, more accurate control of the expansion. In addition, a handle mechanism is provided for adjusting a longitudinal sliding of control wire 21. A threaded drawbar 27 is fastened to the ends of wire 21. A threaded bore inside handle 23 receives drawbar 27. A flange 28 on the end of hollow shaft 26 is captured by a cavity 29 in handle 23 so that handle 23 rotates about its longitudinal axis. Drawbar 27 is keyed to shaft 26 in a manner that prevents its rotation but allows it to move along the longitudinal axis (not shown). Thus, when handle 23 is rotated, drawbar 27 moves inward or outward within the threaded bore according to the direction in which handle 23 is rotated.

Figure 6:
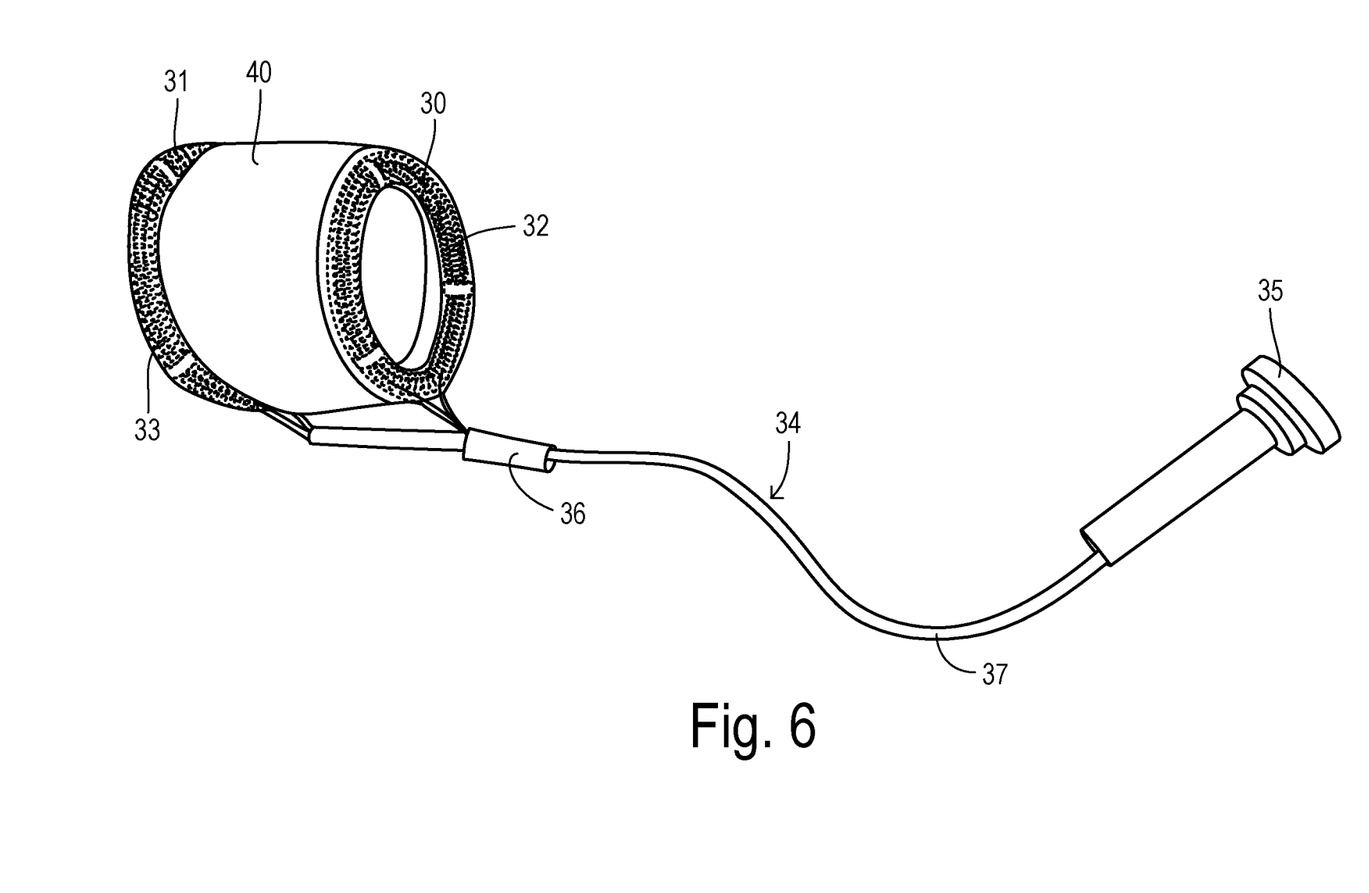
FIG. 6 is a side view of an alternative embodiment using dual rings and a cylindrical sleeve.
Figure 7:
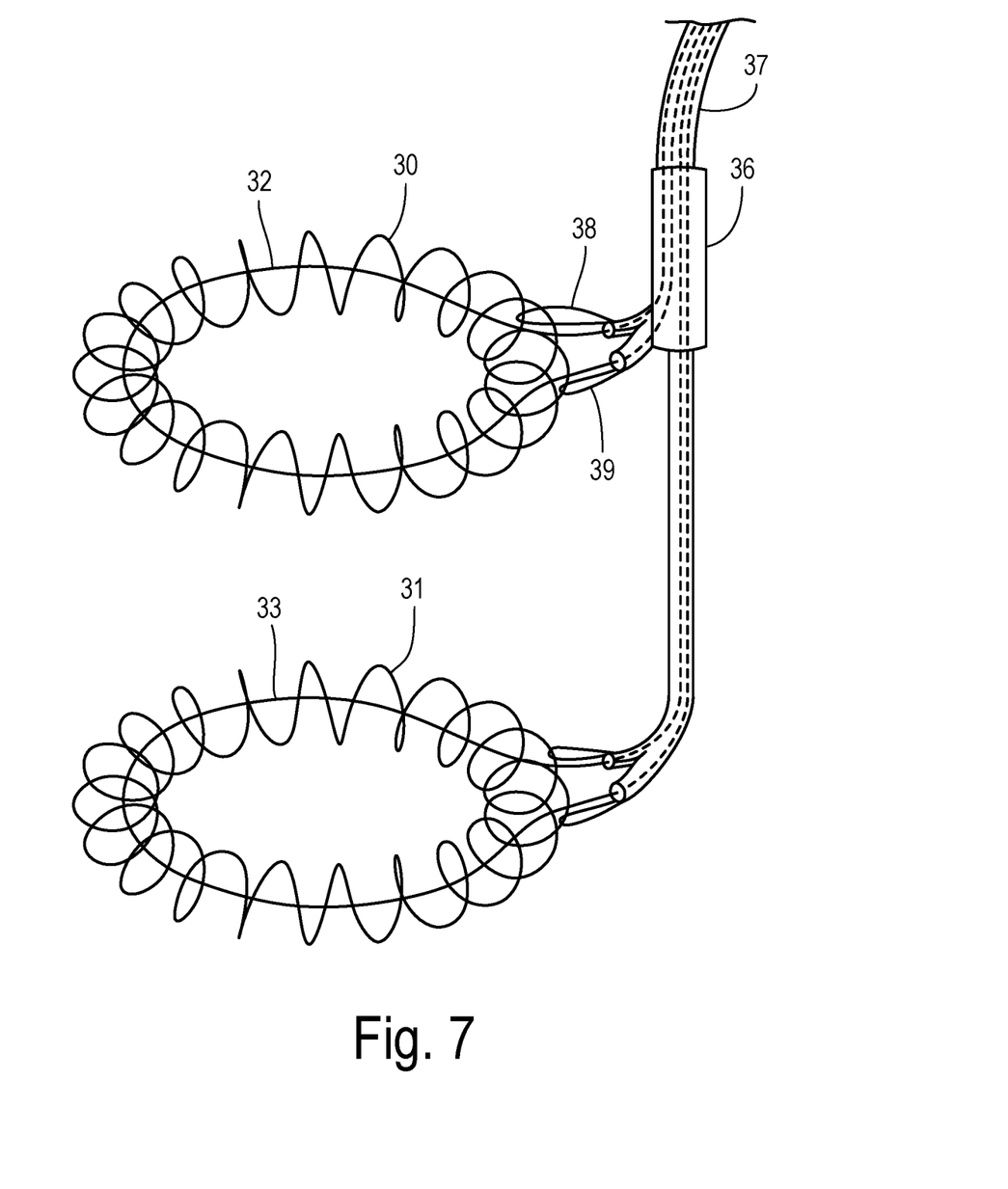
FIG. 7 is a side view showing the dual rings of FIG. 6 in greater detail.
Figure 8:
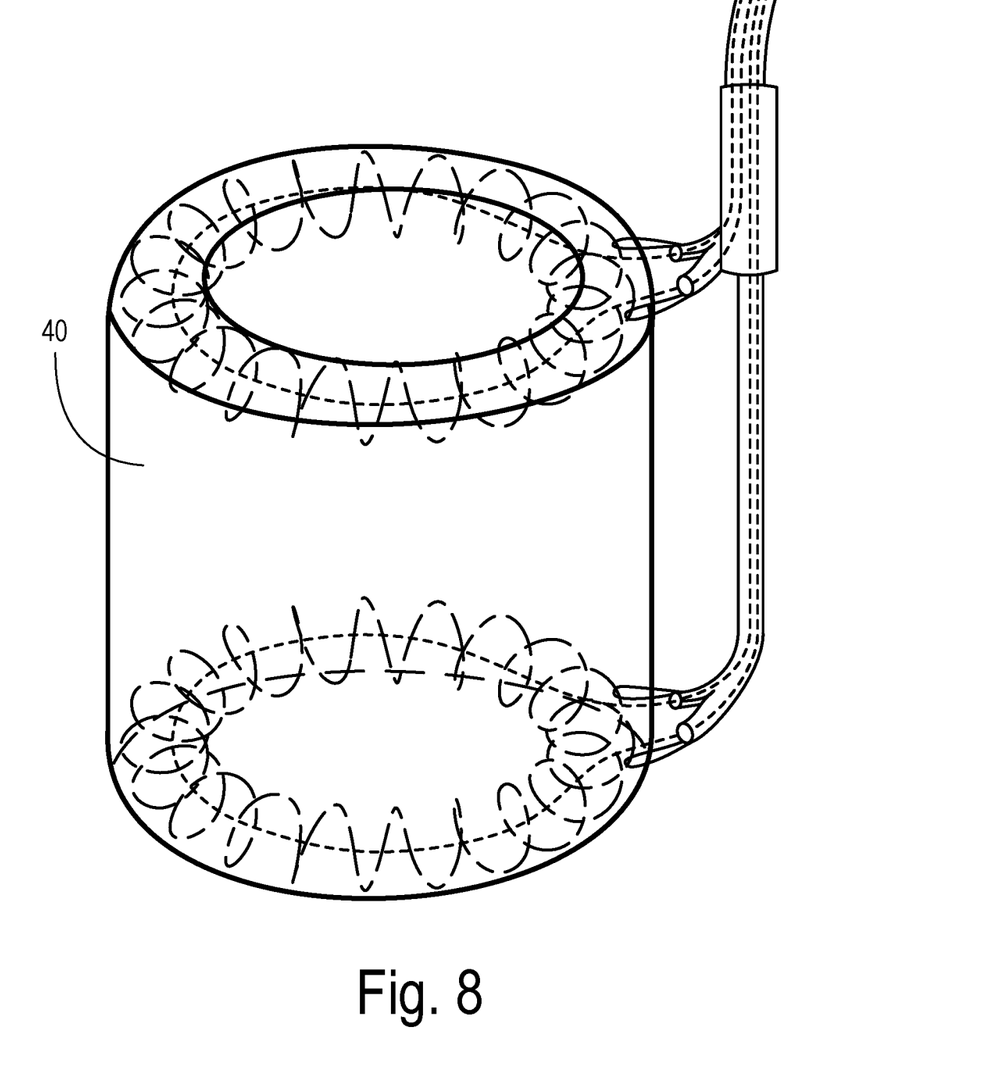
FIG. 8 is a side view showing the sleeve of FIG. 6 in greater detail

FIGS. 6-8 show another embodiment wherein a pair of expandable rings are spaced longitudinally and coaxially to form a cylindrical retractor which can support a valve or vessel structure over an increased depth. A first spring ring 30 and a second spring ring 31 are each formed of a helical coil spring with their ends joined together to assume an expandable toroidal shape. Control wires 32 and 33 have looped ends disposed in rings 30 and 31, respectively. A frame 34 conveys wires 32 and 33 to a handle 35 which may include a knurled knob to facilitate rotation of a mechanism to extend/retract wires 32 and 33. Frame 34 includes Y-arms for each toroidal ring and provides a common exit tunnel for both wires 32 and 33 leading to a malleable hollow tube 37 which is fastened to handle 35. Tethers 38 and 39 anchor rings 30 and 31 to their Y-arms.

A resilient cover 40 provides a retraction sleeve which may have sewn seams at each longitudinal end receiving rings 30 and 31. Cover 40 may be comprised of fabric or a rubber-like material. FIG. 7 shows rings 30 and 31 before installation of cover 40, and FIG. 8 shows cover 40 after installation. The sleeve supports the retracted body structures continuously over a cylindrical surface. Rings 30 and 31 may preferably be spaced by about 40 mm. Handle 35 may contain a dual screw mechanism with separate portions receiving each control wire 32 and 33 so that the size of each ring 30 and 31 can be independently adjusted by rotating separate portions of handle 35. Thus, if the retracted valve has an angled taper shape, the sleeve can be adjusted to match. Also, tube 37 is malleable in order to change shape to allow optimizing the shaft location and avoid interfering with a surgical operation.

Figure 9:
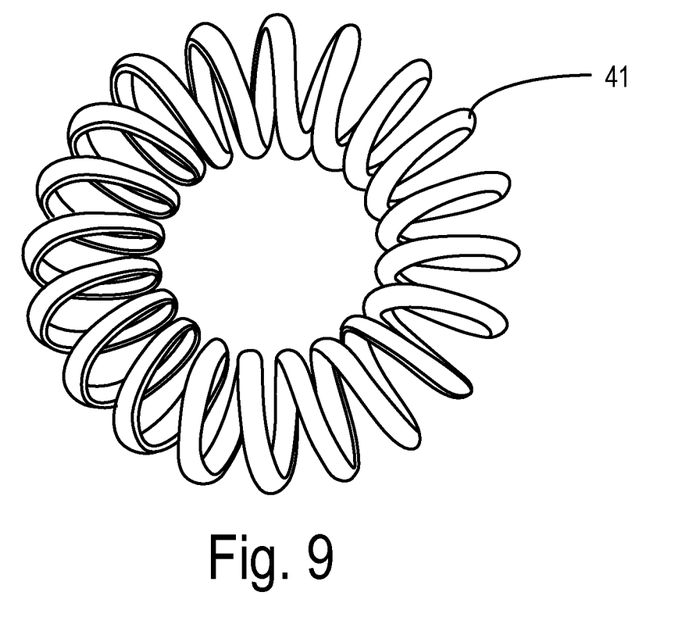
FIG. 9 is a top view of an alternative configuration of a toroidal spring.
Figure 10:
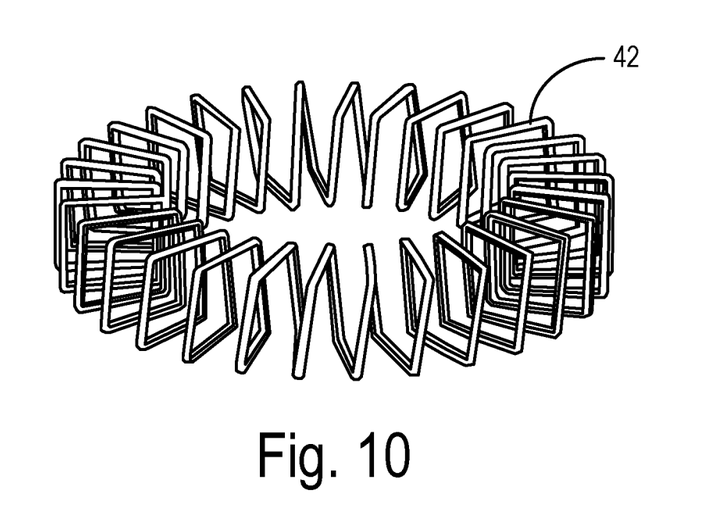
FIG. 10 is a top view of another alternative configuration of a toroidal spring.

FIG. 9 shows a coil spring 41 having circular turns following a toroidal shape using one continuous piece of metal. Since it may be difficult to manufacture a continuous spring having the continuous shape shown in FIG. 9, the same effect can be obtained by bending a helical coil spring with a straight cylindrical shape into a toroid and then joining the opposite ends together (face-to-face) by bonding or by wrapping the ends together using another wire. In addition to circular turns, other spring shapes can be employed. FIG. 10 shows an example wherein the turns of the spring coil have a square profile.

What is claimed is:

1. A surgical retractor for tissue retraction in minimally invasive cardiac surgery, comprising:
   a toroidal ring comprised of a plurality of turns of an expandable helical spring;
   a control wire having a loop end disposed within the turns of the toroidal ring;
   a frame having i) Y-arms at a distal end for guiding the control wire and holding ends of the loop end at an edge of the toroidal ring, and ii) a hollow shaft slidably receiving a proximal end of the control wire; and
   a handle anchored to the proximal end of the control wire and movable with respect to the hollow shaft in order to slide the control wire to expand and contract the loop end, thereby adjusting the ring between an expanded state and a contracted state.

2. The retractor of claim 1 wherein the hollow shaft is malleable.

3. The retractor of claim 1 further comprising a pair of tethers, each tether anchoring a respective Y-arm to a respective turn of the helical spring.

4. The retractor of claim 1 further comprising an adjustment mechanism coupled between the handle and the frame to manually control a relative position between the handle and the frame.

5. The retractor of claim 1 further comprising:
   a second toroidal ring comprised of a plurality of turns of an expandable helical spring;
   a second control wire having a second loop end disposed within the turns of the second toroidal ring;
   a second pair of Y-arms at the distal end of the frame for guiding the second control wire and holding ends of the second loop end at an edge of the second toroidal ring so that the toroidal rings are coaxial and are mutually expandable and contractible.

6. The retractor of claim 5 further comprising:
   a resilient retraction sleeve arranged cylindrically over both of the toroidal rings to support retracted tissue.

7. A surgical retractor for minimally invasive cardiac surgery, comprising:
   a first toroidal rings comprised of a plurality of turns of a first expandable helical spring;
   a second toroidal ring comprised of a plurality of turns of a second expandable helical spring;
   a first control wires having a first loop end disposed within the turns of the first rings;
   a second control wire having a second loop end disposed within the turns of the second ring;

a frame having i) a first pair of Y-arms at a distal end for guiding the first control wire and holding the first loop end at an edge of the first toroidal ring, ii) a second pair of Y-arms at the distal end for guiding the second control wire and holding the second loop end at an edge of the second toroidal ring, wherein the first and second rings are axially spaced to define a cylindrical retraction profile, and iii) a hollow shaft slidably receiving proximal ends of the first and second control wires; and a handle for anchoring the proximal ends of the first and second control wires and movable to independently slide the first and second control wires to expand or contract the first and second loop ends, thereby adjusting the first and second rings between expanded states and contracted states.

8. The surgical retractor of claim 7 wherein the hollow shaft is malleable.

9. The surgical retractor of claim 7 further comprising a plurality of tethers, each tether anchoring a respective Y-arm of the first and second pairs of Y-arms to a respective turn of the respective first and second helical springs.

10. The surgical retractor of claim 7 further comprising an adjustment mechanism coupled between the handle and the frame to manually control a relative position between the handle and the frame.

11. The surgical retractor of claim 7 further comprising:
a resilient retraction sleeve arranged cylindrically over the first and second toroidal rings to support retracted tissue.

\* \* \* \* \*